US00PP09467P

United States Patent [19]

Kent

[11] Patent Number: Plant 9,467

[45] Date of Patent: Mar. 5, 1996

[54] BROMELIAD PLANT NAMED 'GUZ 215'

[75] Inventor: Jeffrey C. Kent, Vista, Calif.

[73] Assignee: Kent's Bromeliad Nursery Inc., Vista, Calif.

[21] Appl. No.: 364,597

[22] Filed: Dec. 27, 1994

[51] Int. Cl.[6] ..... A01H 5/00

[52] U.S. Cl. ..... Plt./88.8

[58] Field of Search ..... Plt./88.8

[56] References Cited

U.S. PATENT DOCUMENTS

P.P. 8,514 12/1993 Bak et al. ..... Plt./88.8

*Primary Examiner*—James R. Feyrer

*Attorney, Agent, or Firm*—Frank B. Robb; Robb & Robb

[57] ABSTRACT

A bromeliad Guzmania having large floral bracts, the lower bracts being light green stained with cream, ruby red obverse and reverse gradually less creamy and ruby red to upper part of the inflorescence, after anthesis the bracts darkening to buff, the cream color being retained for as much as two months.

1 Drawing Sheet

GENERAL DESCRIPTION OF THE INVENTION

This invention relates to bromeliads and more particularly to those bromeliads of the genus known as Guzmania and even more particularly certain limited areas of that family which have been developed by me over a number of years and have been found to be attractive from commercial and decorative standpoints.

As those skilled in the art are aware, bromeliads are known to be within the family bromeliaceae, this plant family including at least 40 genera and probably 900 species among which are Bromelia, Ananas, Tillandsia and others.

These particular plants are tropical American plants and are found in Florida around the Caribbean and in tropical South America generally.

During my experience with bromeliads I have grown many of them in the green house and caused them to be crossed and re-crossed in an effort to produce plants which I feel are attractive for commercial purposes and believe that I have accomplished that and the instant variety described herein is one of those plants.

I designate this particular plant as 'Guz 215', and the application is so entitled therefor.

These plants are epiphytic or terrestrial herbs with regular and perfect bracteate flowers and often have basal and spiny leaves.

The plant family bromeliaceae includes the plant species within which pineapples are classified.

I have grown many varieties of bromeliads and at this particular time am devoting much effort to the Guzmania genus in general and this particular plant hereof falls in that genus.

As will be understood from the fact that I have caused the plant described herein to be selected from a large group of plants grown in greenhouses under my control, I have caused to be selected this particular plant for reasons which will be understood from a consideration of the detailed description following and disclosed in the drawing which shows the particular plant in substantial detail.

BRIEF DESCRIPTION OF THE DRAWING

The single sheet of drawing is a color photograph of the plant of this invention and shows a typical specimen of the plant substantially in side view, with the plant shape depicted. Also illustrated are the mature leaves, and bracts of the inflorescence of the plant 'Guz 215'. The colors depicted are as accurate as is reasonably possible in color photographic depiction's of this type.

Color values presented in this disclosure were taken from the *Horticultural Color Guide* as presented in *Exotica*. Such color definitions are based on the *Dictionary of Color* by Maerz & Paul. Color definitions of ordinary meaning are presented where appropriate and properly descriptive.

BOTANICAL DESCRIPTION OF THE PLANT

I believe the coloration of the bracts of the inflorescence of this plant to be the most novel and distinguishing characteristic of the plant. This characteristic is stable and comes true in progressive serial clonal generations.

I have caused the plant to be asexually reproduced by tissue culture and division under my direction near Vista, Calif., and found that the aforesaid continuing characteristics do in fact follow in the production and growth of these plants.

In order to more clearly delineate the various aspects of this particular plant, I note that it is a Monocot perennial and as such is of an overall height including inflorescence of about 17" to 19" and an overall width in final form of 20" to 22".

The leaves are of relatively common form for the genus and are generally 16 to 18 inches in length and about 1¼" in width meadow green 76.

The floral bracts are linear in shape and have acuminate tips and 6" by 1 and ¼" at the base of the inflorescence, decreasing in size to 2¼" by ¾" at the apex. Lower bracts are meadow green 76 stained with cream and amaranth 40, the obverse and reverse gradually being less creamy and less amaranth 40 to the upper two-thirds of the inflorescence.

Other details of the plant are set forth in the following detailed description and help to delineate the plant and its differences with certain aspects which are important that being desirable to make the plant attractive for commercial purposes which is the basic concept of most plant culture.

Parentage: Sport of Guzmania unknown hybrid, discovered by me several years ago near Vista, Calif.

Classification:

*Botanical.*—Spontaneous Guzmania mutation.

*Commercial.*—Flowering tropical plant of the Guzmania market class.

Method of asexual reproduction: Division and tissue culture.

Plant — general characteristics:

*Type.*—Monocot, perennial.

*Habit.*—Single stem, whorled and closely spaced ascending linear, strap-like leaves with acuminate terminals, typical of hybrids of Guzmania and market class guzmania plants. Lower leaves may droop with age if plant is not timely induced to flower. Terminal portions of most mature leaves may droop in a graceful arch. Internode length and spike length may be more elongated with culture under low light levels or high levels of nitrogen fertilization.

*Hardiness.*—Tender, tropical.

*Size.*—About 20 to 22 inches, or more, in width with the ultimate height of about 17 to 19 inches at optimum blooming induction or determined by timing of gas induction for flowering. Plant height for optimum marketing is about 17 to 19 inches, or taller, including the inflorescence.

*Shape.*—Normally mounded, generally typical of plants of the genus. Leaf placement is whorled forming a rosette.

*Density.*—Leaf spacing is typically close to very close, and typical of hybrids of the market class. Leaf spacing and internode length may increase with culture under low light conditions or when too much nitrogen fertilizer is applied.

*Vigor.*—Considered vigorous.

*Leaves.*—Linear, elongated, ranging to about 16 to 18 inches, or longer as a function of cultural conditions. Leaf width is about one and one-quarter inch. Leaves have acuminate tips. Thickness is about normal for that of plants of this market class. Surfaces are smooth and semi-glossy, meadow green 76. Margins are complete (smooth); leaves are straight when newly formed, but become gently arched when elongated.

Flower buds: Tender, medium in size, long, pointed, and appressed, mimosa 2.

Flowers: Cylindrical corolla, mimosa 2 at anthesis, and scarcely open when receptive, 3/16×15/8.

Floral bracts:

*Upper bracts.*—Cream to white upwards to apex with amaranth 40 and green tips on the upper third. After anthesis the bracts gradually darken to buff but retaining its cream color for two months.

Reproductive organs: Six stamens, two joined to each petal ¼ of the distance from the base, stigmata white, sterile $F^1$ hybrid.

I claim:

1. A new and distinct Guzmania plant, substantially as herein shown and described, characterized particularly as to novelty by the floral bracts of linear acute form about six inches by one and one-quarter inches decreasing in size to two and one quarter by three-quarter inches at the apex, the lower bracts being light green stained with cream and ruby red, the obverse and reverse, gradually less cream and ruby red to the upper two-thirds of the inflorescence, after anthesis the bracts gradually darken to buff, retaining the cream color for about two months.

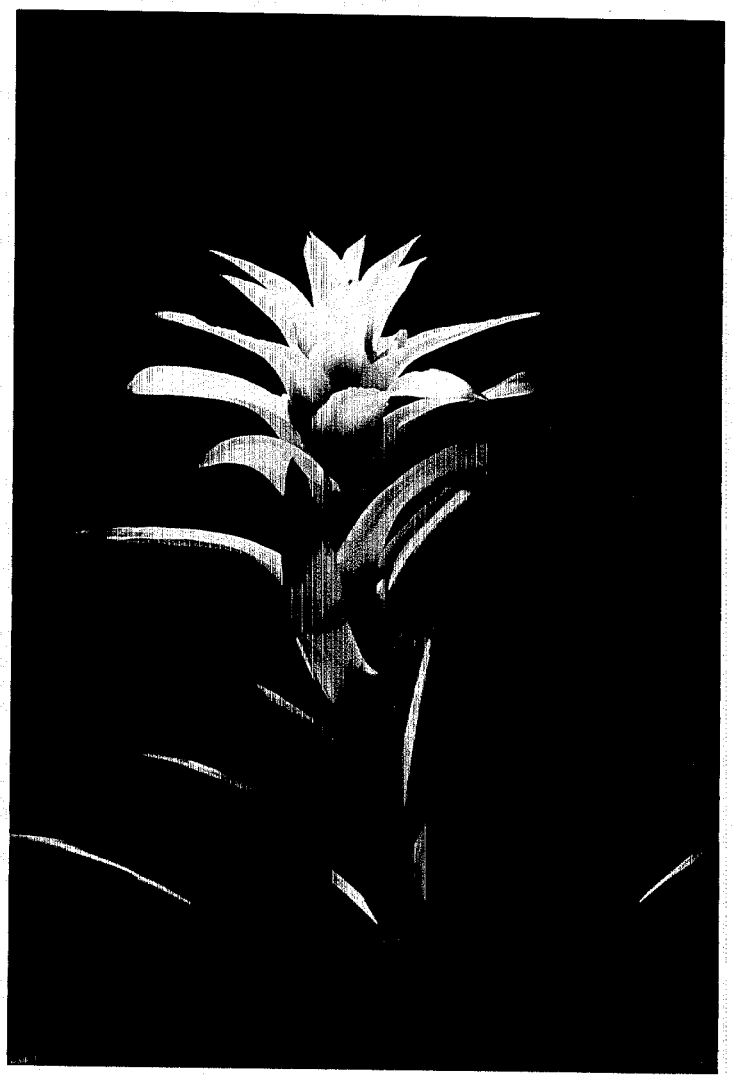

* * * * *